US008042684B2

(12) United States Patent
Guenter et al.

(10) Patent No.: US 8,042,684 B2
(45) Date of Patent: Oct. 25, 2011

(54) RECEIVING ELEMENT FOR A DENTAL IMPLANT

(75) Inventors: Daniel Guenter, Waldenburg (CH); Rainer Bammerlin, Kandem (DE)

(73) Assignee: Straumann Holding AG, Basel (CH)

( * ) Notice: Subject to any disclaimer, the term of this patent is extended or adjusted under 35 U.S.C. 154(b) by 0 days.

(21) Appl. No.: 12/602,687

(22) PCT Filed: Jun. 5, 2008

(86) PCT No.: PCT/EP2008/056997
§ 371 (c)(1),
(2), (4) Date: Dec. 2, 2009

(87) PCT Pub. No.: WO2008/148843
PCT Pub. Date: Dec. 11, 2008

(65) Prior Publication Data
US 2010/0173261 A1    Jul. 8, 2010

(30) Foreign Application Priority Data
Jun. 5, 2007 (DE) .......................... 10 2007 026 504

(51) Int. Cl.
*A61B 19/02* (2006.01)
*B65D 83/10* (2006.01)
*A61C 8/00* (2006.01)
(52) U.S. Cl. .................. 206/63.5; 206/368; 433/173
(58) Field of Classification Search .................. 206/63.5, 206/368, 369, 438, 446; 433/163, 172–176
See application file for complete search history.

(56) References Cited

U.S. PATENT DOCUMENTS

| 6,261,097 | B1 * | 7/2001 | Schmutz et al. | 433/173 |
| 7,207,801 | B2 * | 4/2007 | Vogt et al. | 433/173 |
| 7,338,286 | B2 * | 3/2008 | Porter et al. | 433/173 |
| 2004/0112781 | A1 * | 6/2004 | Hofverberg et al. | 206/438 |
| 2005/0035015 | A1 * | 2/2005 | Bressler et al. | 206/368 |
| 2006/0269890 | A1 * | 11/2006 | Mundwiler et al. | 433/13 |
| 2007/0072148 | A1 * | 3/2007 | Memmolo et al. | 433/173 |
| 2007/0193905 | A1 * | 8/2007 | Jemelin et al. | 206/438 |

FOREIGN PATENT DOCUMENTS

| DE | 203 04 757 U 1 | 7/2003 |
| EP | 1 447 056 A2 | 8/2004 |
| WO | WO 98/55039 | 12/1998 |
| WO | WO 02/30315 A1 | 4/2002 |
| WO | WO 2005/037126 A1 | 4/2005 |

* cited by examiner

*Primary Examiner* — Bryon Gehman
(74) *Attorney, Agent, or Firm* — Scully, Scott, Murphy & Presser, P.C.

(57) ABSTRACT

A receiving element for a dental implant is provided. The receiving element has a hollow body extending along a center axis of the receiving element, and a first plate and a second plate extending substantially perpendicular to the center axis of the receiving element and configured to fix a dental implant releasably in a stable position. The first plate and the second plate each has a front end, a rear end opposite to the front end, a first lateral end and a second lateral end opposite to the first lateral end. The receiving element further has an open portion disposed between the first plate and the second plate to partially separate the first plate and the second plate. The open portion extends from the front end substantially up to the center axis of the receiving element. The open portion has a first gap extending from the first lateral end substantially up to the center axis and a second gap extending from the second lateral end substantially up to the center axis, each gap allowing communication along the entire length thereof between an interior of the body and an exterior of the body.

11 Claims, 3 Drawing Sheets

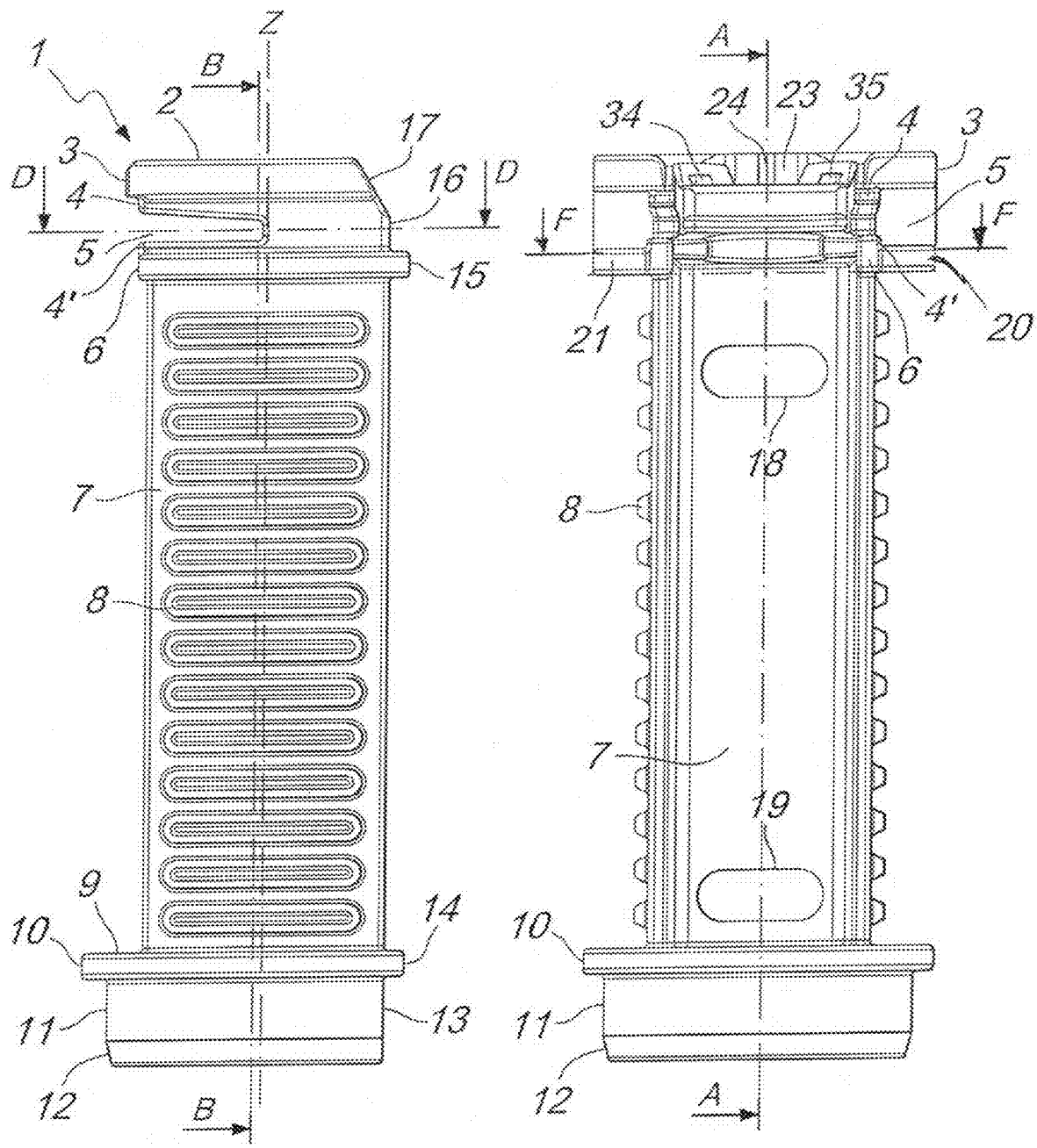

RECEIVING ELEMENT FOR A DENTAL IMPLANT

FIELD OF USE OF THE INVENTION

The present invention relates to a receiving element for an implant, in particular for screw- or cylinder-shaped implants.

Such implants are already known e.g. from dental technology and are substantially similar to a screw, the apical area of the screw being inserted in a bone and the coronal area being suitable to receive a dental prosthesis. In addition, in dental surgery, different embodiments of holding elements fastened to the implant are known which, on the one hand, fix the implant into place and, on the other hand, allow sterile removal from the receiving element. In addition, they also ensure that from manufacturing until surgical intervention, an implant does not come in contact with non-sterile means, such as hands. The relevant area of application for the invention is where the implants, e.g. for reasons of necessary sterile handling, may at least not directly be touched with one's hands, and where secure grasping of the implants is required.

The function of such receiving elements is to transport the implant safely and provide a sterile environment for storage. To remove the implant during a surgical intervention performed under sterile conditions, the implant is taken from the receiving element which generally has a holding element fastened to the implant (in the following, the combination of implant and holding element attached to it will be called implant assembly for simplification), e.g. by means of a tool applied to the implant, and the implant is subsequently placed on the prepared implant site of the patient and the holding element is removed. For further protection, it is also common to store the receiving element in a secondary protection element until the time of implanting.

PRIOR ART

From WO98/55039, a cylindrical ampule to be inserted in an outer capsule is known, which ampule is suitable for receiving an implant. The ampule has a face region provided with an recess which is laterally open. This recess is used to insert an implant assembly consisting of the implant and a holding element additionally connected to the implant. The implant assembly is fixed into place in a throat of the ampule by being pressed through an opening. To achieve sufficient fixation, substantial pressure must be applied when the implant is pressed in; with a rigid structure of an ampule and a receiving element, the consequence is that the construction material is subjected to substantial stress, since the forces that occur spread both along the expansion groove and along the cylinder surface. There is a danger of cracks formation on the face side in case of pressure which is too strong, which cracks can reduce or even offset the clamping effect within the throat. Furthermore, due to the rigid construction, insertion is only possible by using great force if the recess has only a small aperture angle, since expansion can only take place within the area of the expansion groove, which is relatively narrow, and the cylinder surface further impedes expansion. An enlargement of the aperture angle of the recess facilitates insertion of the dental implant, however at the cost of a good clamping behavior, so that the implant can easily slide out of the recess and touch non-sterile surfaces. Even worse, the implant can also be damaged if, for instance, it falls down from the operating table to the floor. Also, the face side of the ampule has a relatively small cross-section, and the entire holding force between an implant and the interior of the throat is limited to this narrow area, the holding force or withdrawal force, respectively, being consequently increased by the pressure or compression, respectively, when the implant is removed from the holder. This increases the grip on the implant, making the removal process difficult to control.

In addition, storage over a longer time can lead to a weakening at the clamping area which, in the worst case, can cause the implant to be no longer held with full clamping force, making it oscillate within the ampule so that it can be damaged by contact with the ampule.

Furthermore, if deposited, the cylindrical ampule can move about its axis within a certain range, which makes it difficult to grip.

SUMMARY OF THE INVENTION

In view of the above-mentioned drawbacks of the prior art devices for receiving a dental implant, the object of the present invention is to provide a receiving element for a dental implant which fixes a dental implant assembly in place more secure and which can better convert and carry off the forces occurring when the dental implant assembly is placed on the structure of the receiving element. Furthermore, simpler and safer handling should be provided and economical manufacturing with existing techniques should be possible.

The object of the present invention is to provide a receiving element for a dental implant having improved stability and conversion of forces and which avoids the drawbacks mentioned above.

Within this aim, another object of the present invention is to provide a receiving element for a dental implant which is better protected against slipping on a surface.

Another object of the present invention is that the receiving element can be handled more easily and more safely.

Another object of the present invention is that the receiving element can be manufactured easily and inexpensively with well-known methods.

This aim and these and other objects to be found in the following specification are fulfilled by a receiving element for a dental implant according to Claim 1. Other advantageous embodiments of the present invention are the subject matter of the dependent claims.

The constructive characteristics of a substantially cylindrical receiving element according to the present invention consist in that the head area holding the receiving element is nearly uncoupled from the body so that forces occurring during removal of the dental implant from the holder through the aperture provided for this purpose are effectively diverted and/or completely eliminated. The substantially square body portion is advantageously provided with an open side for easy insertion of the dental implant. Furthermore, the head area has a first surface suitable for clamping connection with a dental implant and a second surface which prevents the dental implant from touching the interior wall of the body part.

Furthermore, one side of the receiving element is provided with a plane surface ensuring stable positioning on a surface such as the operating table. In a preferred embodiment, the receiving element has a plurality of reinforcing ribs in its body area which, on the one hand, reinforce the outer wall and, on the other hand, ensure a better grip.

SHORT DESCRIPTION OF THE FIGURES

Further features and advantages of the present invention as well as the operating method of the exemplary embodiments of the present invention are described below with reference to the accompanying drawings.

The accompanying drawings illustrate the present invention and, together with the specification, are used to explain the basics of the invention and to enable a person skilled in the relevant art to manufacture and use the invention. For better comprehensibility, identical elements are for the most part not designated in the following figures as long as they can be clearly recognized as "repeated elements".

Therein:

FIG. 1 shows a side view of a receiving element for a dental implant according to an embodiment of the invention;

FIG. 2 shows a front view of a receiving element for a dental implant according to FIG. 1;

DESCRIPTION OF PREFERRED EMBODIMENTS OF THE INVENTION

Figure 3:
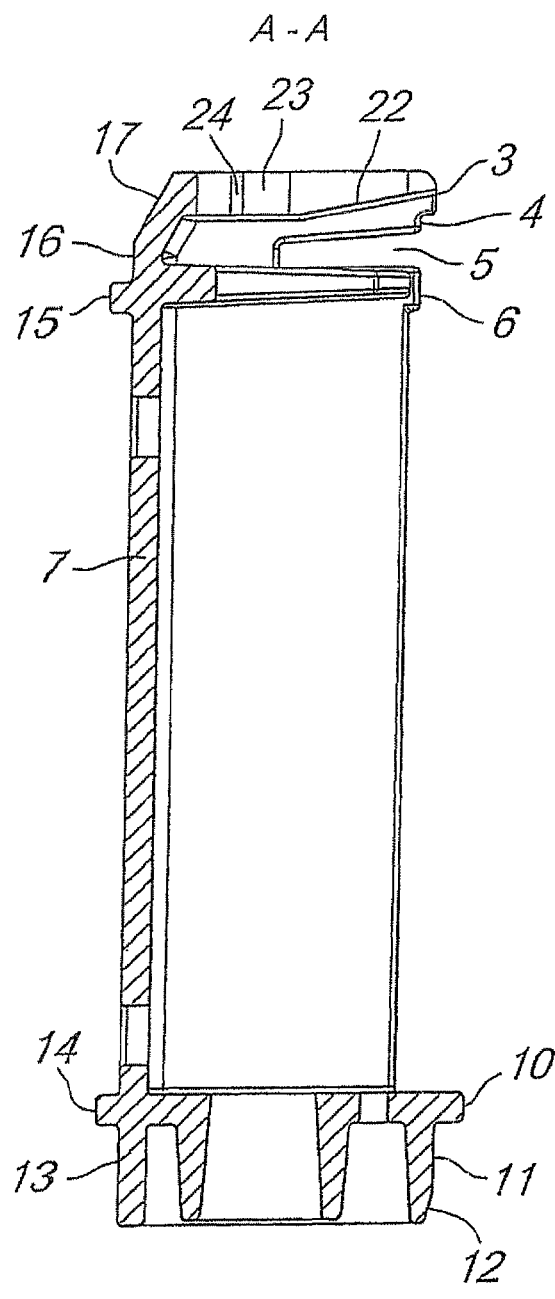
FIG. 3 shows a longitudinal section of a receiving element for a dental implant according to FIG. 1, taken along line A-A in the direction of the arrow.

Based on FIG. 1 to FIG. 7, a currently preferred embodiment of the present invention of a receiving element for a dental implant is described, which element consists of a substantially cylindrical bottom area, a body area enclosing the dental implant and a flexible head area formed by two plates, the head area being provided with a clamping device for receiving a dental implant, which device is suitable for releasably clamping and fixing a dental implant into place.

FIG. 1 shows a receiving element 1 for a dental implant, the receiving element 1 basically having three portions. A first portion forming the head area consists of an approximately C-shaped, plane front face 2 comprising a first plate 3 which is suitable for fixing a dental implant (not shown) into place, as is described further in the foregoing. The first plate 3 is adjacent to an open area 5 surrounded by a first shoulder 4 bordering on the first plate 3 and a second shoulder 4' below it which borders on a second plate 6. The open area 5 which is preferably jaw-shaped preferably extends from its open side at a respective end of the plates 3, 6 to a theoretical center axis Z of the receiving element 1, the opening width in the area of the center axis Z being advantageously smaller than on the outer side. The jaw-like area 5 achieves a mechanical uncoupling of the plates 3, 6 and of the first plate 3 from the body 7, respectively.

On the side which is not provided with the jaw-like area 5, a chamfer 17 from an outer edge of the plane front face 2 to a plane head area 16 is provided, the plane head area 16 bordering on a plane head edge 15 which borders both on the head area 16 and on a body 7 of the receiving element 1. Part of the second plate 6 which borders on the jaw-like open area 5 and on the second shoulder 4', respectively, is substantially plane. The part of the second plate 6 which is below the jaw-like area 5 then borders on a second portion formed by the body 7 and provided with a plurality of symmetrically arranged reinforcing ribs 8. These protrude from the surface of the body 7 and are preferably arranged equidistant from one another. In the preferred embodiment, these reinforcing ribs 8 have a longitudinal shape. A base surface 9 borders on the edge of the body 7 opposite to the second plate 6, which base surface is substantially symmetrically round and on which the body 7 is arranged perpendicularly. The third portion comprises a perimetric surrounding edge 10 embedded between the base surface 9 and a bottom part 11, with the bottom part 11 transitioning on one side into the standing area 12 which is suitable for the placement on a surface. A bottom portion 13 formed between the bottom edge 14 and the standing area 12 is preferably plane. The bottom edge 14 which is also plane borders on the bottom portion 13. Due to the plane embodiment of the head edge 15 and of the bottom edge 14, it is possible to position the receiving element 1 stably on a surface and to both prevent it from rolling away and to grip it easily.

Figure 7:
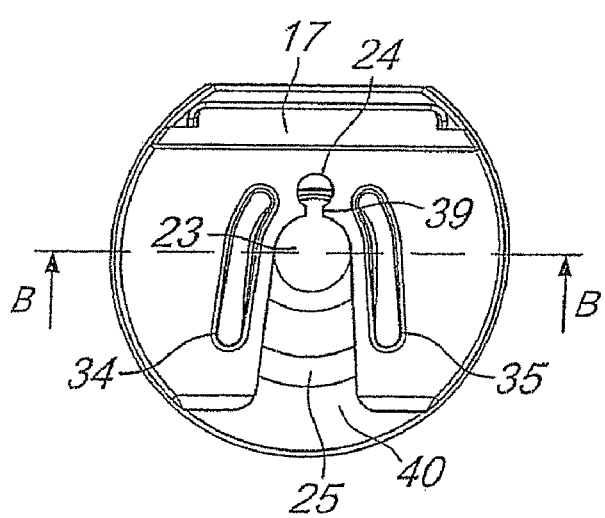
FIG. 7 shows a top view of a receiving element for a dental implant according to FIG. 1.

FIG. 2 shows further features of the receiving element 1, a first through hole 23 and a second through hole 24 being arranged in the center of the first plate 3. The second through hole 24 can preferably have a smaller diameter than the first through hole 23, although in the presently preferred embodiment the difference in diameter is not indispensable. The first through hole 23 and the second through hole 24 are, in one place, connected to each other by an open groove 39 as is also shown in FIG. 7. The first through hole 23 borders on an opening 40, see FIG. 7, of the first plate 3. Furthermore, a first elongated hole 18 and a second elongated hole 19 are provided in the body 7 as can be seen in FIG. 2.

Figure 4:
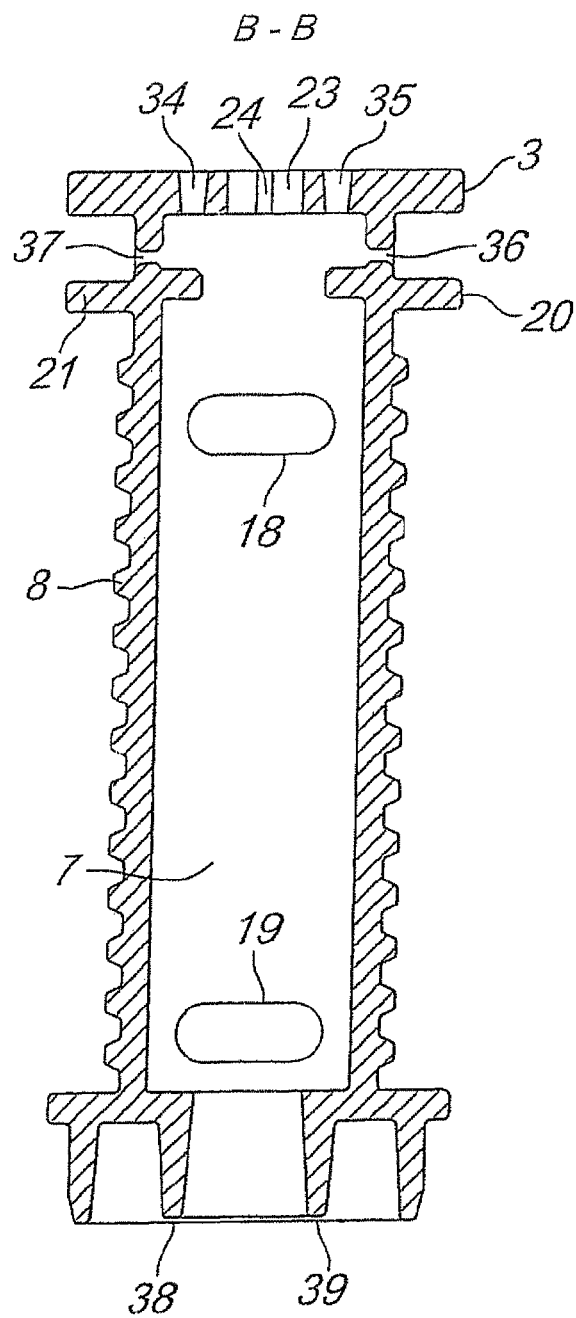
FIG. 4 shows a longitudinal section of a receiving element for a dental implant according to FIG. 1, taken along line B-B in the direction of the arrow.

FIG. 3 and FIG. 4 show additional features of the receiving element 1, a portion of the first plate 3 being provided with a chamfered leg 22 which extends from the outer edge approximately up to the area of a theoretical center axis Z of the receiving element 1, the chamfered leg 22 allowing an easy insertion of a dental implant. Furthermore, when the dental implant is pressed in, the first plate 3 can be elastically deformed with respect to the second plate 6 in a direction perpendicular to the center axis Z of the receiving element 1 until the dental implant is locked into place in the first through hole 23 and held there clampingly, a first gap 36 and a second gap 37 of the jaw-like portion 5 mechanically uncoupling the first plate 3 from the body 7 and from the second plate 6, respectively, as mentioned above. In addition, the chamfer 17 on the opposite side advantageously has a resilient effect. A first reinforcement 20 and a second reinforcement 21 are used to strengthen the construction against the tensions produced when the dental implant is pressed in. A first notch 34 and a second notch 35 which can have a conical shape and which are arranged symmetrically in the first plate 3 and adjacent to the first through hole 23 and the second through hole 24 are suitable for distributing the forces when the dental implant is pressed in through the opening 40 of the first plate 3, and the first plate 3 can be expanded elastically in a direction perpendicular to the center axis Z. The conical shape of the notches is preferred especially for machining reasons if the receiving element is manufactured by injection molding. As mentioned above, the second through hole 24 has a smaller diameter than the first through hole 23 and is connected to it by the groove 39 so that the through hole 24 is used as an expansion through hole and can be enlarged when a dental implant is pressed in. The elastic deformability of the first plate 3 advantageously results both in a clamping and in a snap-in connection which securely fixes the dental implant in the first through hole 23.

Figure 5:
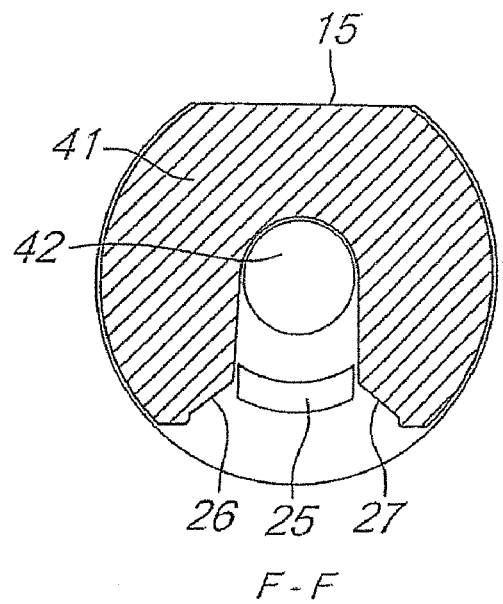
FIG. 5 shows a sectional view of a receiving element for a dental implant according to FIG. 1, taken along line F-F in the direction of the arrow.
Figure 6:
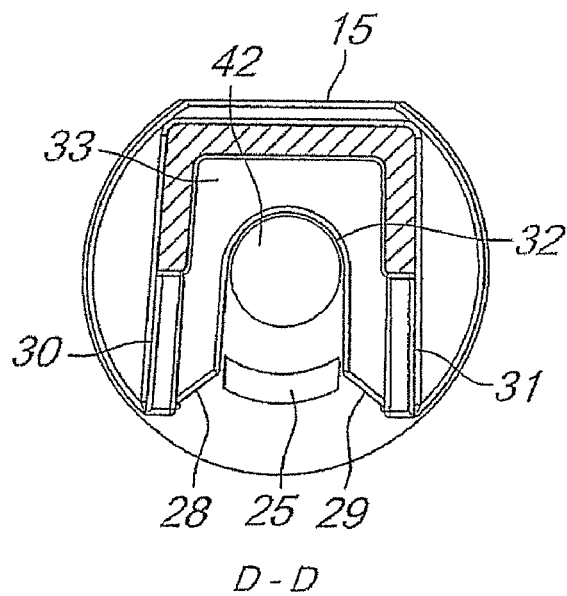
FIG. 6 shows a sectional view of a receiving element for a dental implant according to FIG. 1, taken along line D-D in the direction of the arrow.

FIG. 5 and FIG. 6 show the head area of the receiving element 1, FIG. 5 showing an area 41 which has, in the portion of the opening 40, see FIG. 7, a first chamfer 26 and a second chamfer 27 used for easy insertion of the dental implant. The angle between the first and the second chamfer is preferably within a range of 80 to 120 degrees. The area 41 which is enclosed over the entire cross-section up to the chamfers 26, 27 is rigid so as to form the U-shaped portion 32 shown in FIG. 6. The inner surface of the U-shaped portion 32 forms a stopping portion 33 in which an inserted dental implant is kept in a stable position so that contact with the interior walls of the body 7, e. g. during transport, is excluded. In the portion of the opening 40, the base surface 9 from FIG. 1 has an annular portion 25 having approximately the width of the U-shaped portion 32 and, in its center, the base surface has a third through hole 42 with a larger diameter than the first and the second through hole 23, 24.

FIG. 7 shows that the first through hole 23 is aligned with the third through hole 42. Within the area of the opening 40, the first notch 34 and the second notch 35 extend substantially parallel thereto, slightly curving in the direction of the center of the second through hole 24 near the first 23 and the second 24 through hole.

The receiving element 1 can be manufactured with conventional processes, e. g. casting, and is preferably made of an elastic plastic material.

If technical features mentioned in any claim are provided with a reference number, these reference numbers have been merely included to increase comprehensibility of the claims. Accordingly, these reference numbers have no limiting effect on the scope of each element identified by way of example by such reference numbers.

LIST OF REFERENCE NUMBERS 1 receiving element
2 front face
3 first plate
3 first shoulder
4' second shoulder
5 jaw-like portion
6 second plate
7 body
8 reinforcing ribs
9 base surface
10 surrounding edge
11 bottom part
12 standing area
13 plane bottom portion
14 bottom edge
15 head edge
16 plane head area
17 chamfer
18 first elongated hole
19 second elongated hole
20 first protrusion
21 second protrusion
22 chamfered leg
23 first through hole
24 second through hole
25 annular portion
26 first chamfer
27 second chamfer
28 first insertion edge
29 second insertion edge
30 first guide rail
31 second guide rail
32 stopping portion
33 U-shaped portion
34 first notch
35 second notch
36 first gap
37 second gap
38 cylindrical interior wall
39 groove
40 opening
41 area
42 third through hole

The invention claimed is:

1. A receiving element for a dental implant, comprising:
   a hollow body extending along a center axis of the receiving element;
   a first plate and a second plate extending substantially perpendicular to the center axis of the receiving element and configured to fix a dental implant releasably in a stable position, the first plate and the second plate each comprising a front end, a rear end opposite to the front end, a first lateral end and a second lateral end opposite to the first lateral end; and
   an open portion disposed between the first plate and the second plate to partially separate the first plate and the second plate, the open portion extending from the front end substantially up to the center axis of the receiving element, the open portion comprising a first gap extending from the first lateral end substantially up to the center axis and a second gap extending from the second lateral end substantially up to the center axis, each gap allowing communication along the entire length thereof between an interior of the body and an exterior of the body, wherein:
   the first plate is elastic to ensure a clamping accommodation of a dental implant in an opening of the first plate, and
   the second plate has a substantially U-shaped stopping portion formed to stabilize the position of an inserted dental implant.

2. The receiving element for a dental implant according to claim 1, wherein the open portion is tapered from the front end to the center axis when viewed laterally.

3. The receiving element for a dental implant according to claim 1, wherein the second plate is rigid and provides a guide for the dental implant.

4. The receiving element for a dental implant according to claim 1, wherein the first plate is elastically deformable in the direction of the center axis of the receiving element.

5. The receiving element for a dental implant according to claim 1, wherein the first plate is elastically deformable in a direction perpendicular to the center axis of the receiving element.

6. The receiving element for a dental implant according to claim 1, wherein the first plate has a first through hole and a second through hole adjacent to the opening, the second through hole having a smaller diameter than the first through hole and the first and the second through holes being interconnected by a groove.

7. The receiving element for a dental implant according to claim 1, wherein the first plate has symmetrically arranged notches which are preferably arranged around the opening.

8. The receiving element for a dental implant according to claim 1, wherein the body comprises a plurality of grip elements.

9. The receiving element for a dental implant according to claim 8, wherein the body has a substantially square cross-section.

10. The receiving element for a dental implant according to claim 1, wherein the receiving element is formed from an elastically deformable plastic material.

11. The receiving element for a dental implant according to claim 1, wherein the body comprises a plurality of reinforcing elements.

* * * * *